(12) United States Patent
Nattrass

(10) Patent No.: US 6,218,177 B1
(45) Date of Patent: Apr. 17, 2001

(54) VENTILATION FOR ORGANIC MATTER BREAKDOWN

(75) Inventor: Nigel Nattrass, Rhodes (AU)

(73) Assignee: L N Nattrass Trading PTY Ltd. (AU)

( * ) Notice: Subject to any disclaimer, the term of this patent is extended or adjusted under 35 U.S.C. 154(b) by 0 days.

(21) Appl. No.: 09/230,794

(22) PCT Filed: Aug. 7, 1997

(86) PCT No.: PCT/AU97/00501

§ 371 Date: May 3, 1999

§ 102(e) Date: May 3, 1999

(87) PCT Pub. No.: WO98/05606

PCT Pub. Date: Feb. 12, 1998

(30) Foreign Application Priority Data

Aug. 7, 1996 (AU) .................................................. 1499

(51) Int. Cl.$^7$ .................................................. C12M 1/00
(52) U.S. Cl. .................................................. 435/290.1; 435/818
(58) Field of Search ............................ 435/290.1, 290.2, 435/290.4, 818

(56) References Cited

U.S. PATENT DOCUMENTS 4,105,412 * 8/1978 Petzinger .
5,429,945 * 7/1995 Shain .

FOREIGN PATENT DOCUMENTS

| 120637 | 7/1994 | (AU) . |
| 7750476 | 6/1977 | (CH) . |
| 86119488 | 1/1986 | (DD) . |
| 7562485 | 9/1975 | (DE) . |
| 86205621 | 8/1986 | (DE) . |
| 88127327 | 5/1988 | (DE) . |
| 91110412 | 4/1991 | (DE) . |
| 91282361 | 9/1991 | (DE) . |
| 96385766 | 10/1996 | (DE) . |
| 97272846 | 4/1997 | (DE) . |
| 95 35182 | 10/1995 | (FR) . |
| 8240795 | 1/1982 | (SE) . |
| 468944 | 4/1993 | (SE) . |
| 93285948 | 6/1993 | (SE) . |
| 95310265 | 6/1996 | (SE) . |

* cited by examiner

Primary Examiner—David A. Redding
(74) Attorney, Agent, or Firm—Ostrolenk, Faber, Gerb & Soffen, LLP

(57) ABSTRACT

In a container (1) for breaking down organic matter and/or breeding worms, enhanced ventilation is provided via legs (7) which support the container above the ground. Each leg has a longitudinal open channel-like duct which may be formed by making the legs hollow and semi-circular. Each duct communicates with the interior of the container (1) so that any breeze impinging upon the duct causes air to flow upwardly into the container. The effect is enhanced by orienting the legs in different directions and providing air outlets (19) in the lid (6) of the container.

10 Claims, 3 Drawing Sheets

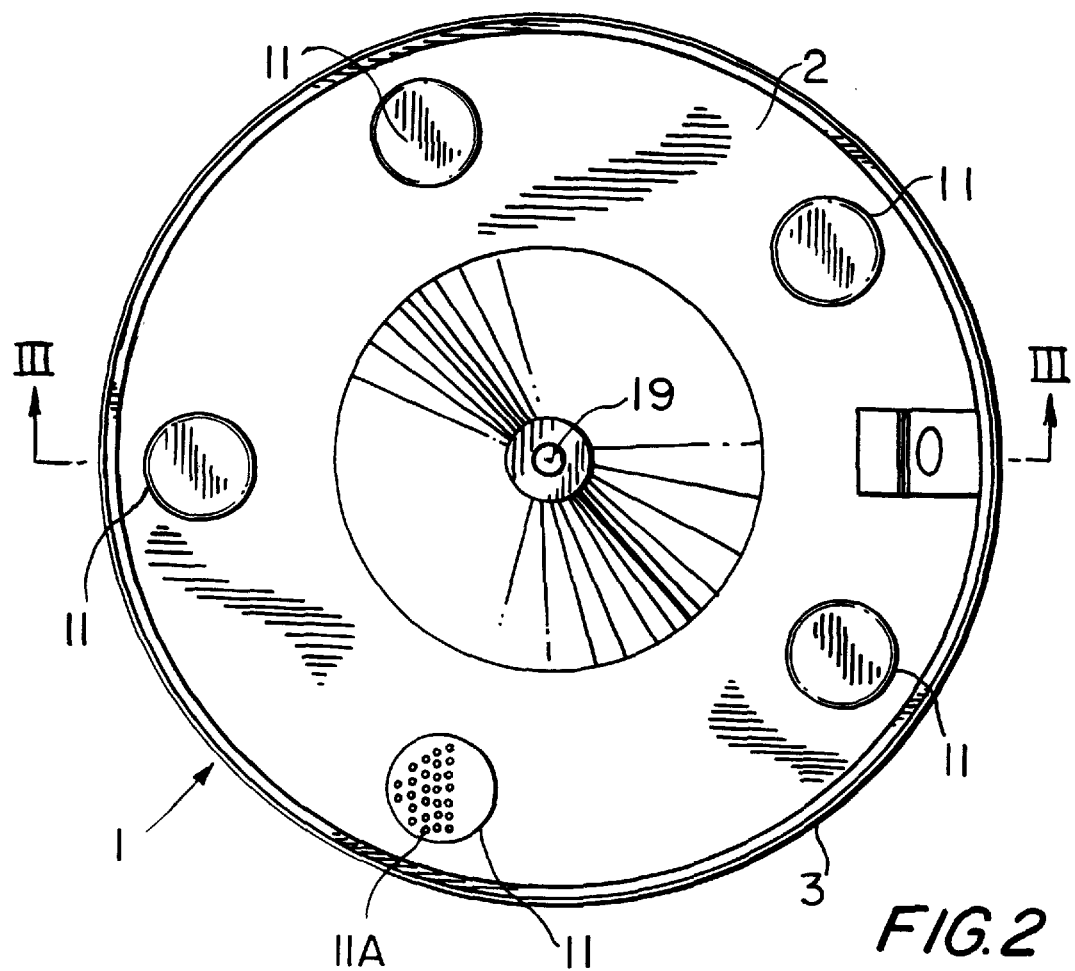
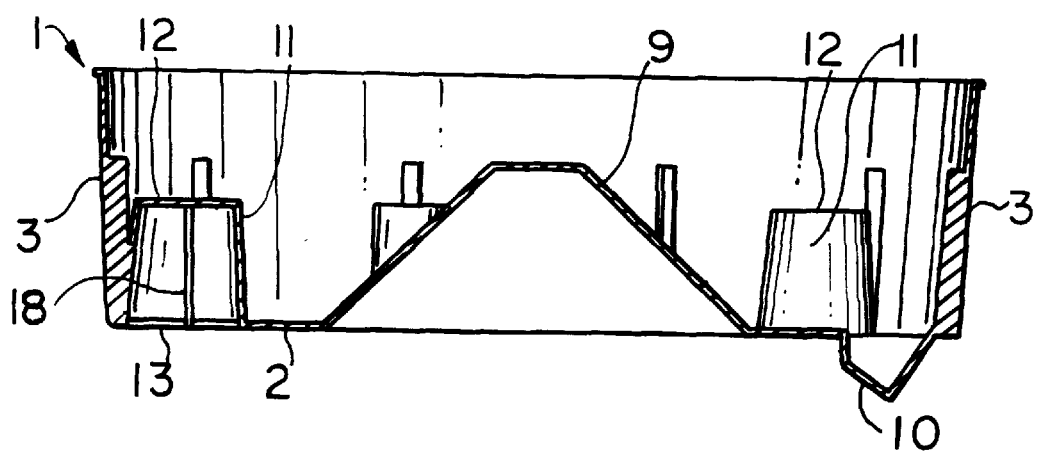
FIG.2
FIG.3

VENTILATION FOR ORGANIC MATTER BREAKDOWN

TECHNICAL FIELD

This invention relates to ventilation for organic matter breakdown and has been devised particularly though not solely for the ventilation of closed containers used for composting and/or the breeding of worms.

BACKGROUND ART

There are many situation in which closed containers, typically drums or bins are used for composting organic material such as kitchen or garden waste either as a simple composting operation or when assisted by the action of earthworms, whether the prime purpose of the operation is for breaking down the organic matter or for the breeding of worms. Such apparatus is described in the specification of Australian patent application number 58295/94.

It is desirable to provide a degree of ventilation to such containers to assist the aerobic breakdown of the organic matter within the container and such ventilation is typically provided by way of screened vents in the lid and/or sides of such containers. It is however desirable to provide an enhanced level of ventilation which will capture breezes blowing over the container and direct the air into the container in a manner and location which is particularly conductive to aerobic breakdown and to the breeding of worms within the container.

DISCLOSURE OF THE INVENTION

The present invention therefore provides apparatus for breaking down organic matter comprising a container having a case and upwardly extending peripheral side walls, supported on a plurality of legs, characterised by the provision of an open channel-like duct within each leg, each leg being mounted to the container such that air can flow from the duct to the interior of the container, providing ventilation.

Preferably each leg is mounted in a corresponding socket in the base of the container.

Preferably each socket has one or more openings in the upper part thefeof allowing air to pass from the duct in a leg engages in the socket, into the container.

Preferably the openings comprise an array of foramina sized to allow air flow while inhibiting the ingress of insects.

BRIEF DESCRIPTION OF THE DRAWINGS

Notwithstanding any other forms that may fall within its scope, one preferred form of the invention will now be described with reference to the accompanying drawings, in which:

FIG. 2 is an underside view of the lowermost container incorporated in the apparatus shown in FIG. 1;

FIG. 3 is a cross sectional elevation on the line III—III of FIG. 2;

BEST MODES FOR CARRYING OUT THE INVENTION

Figure 1:
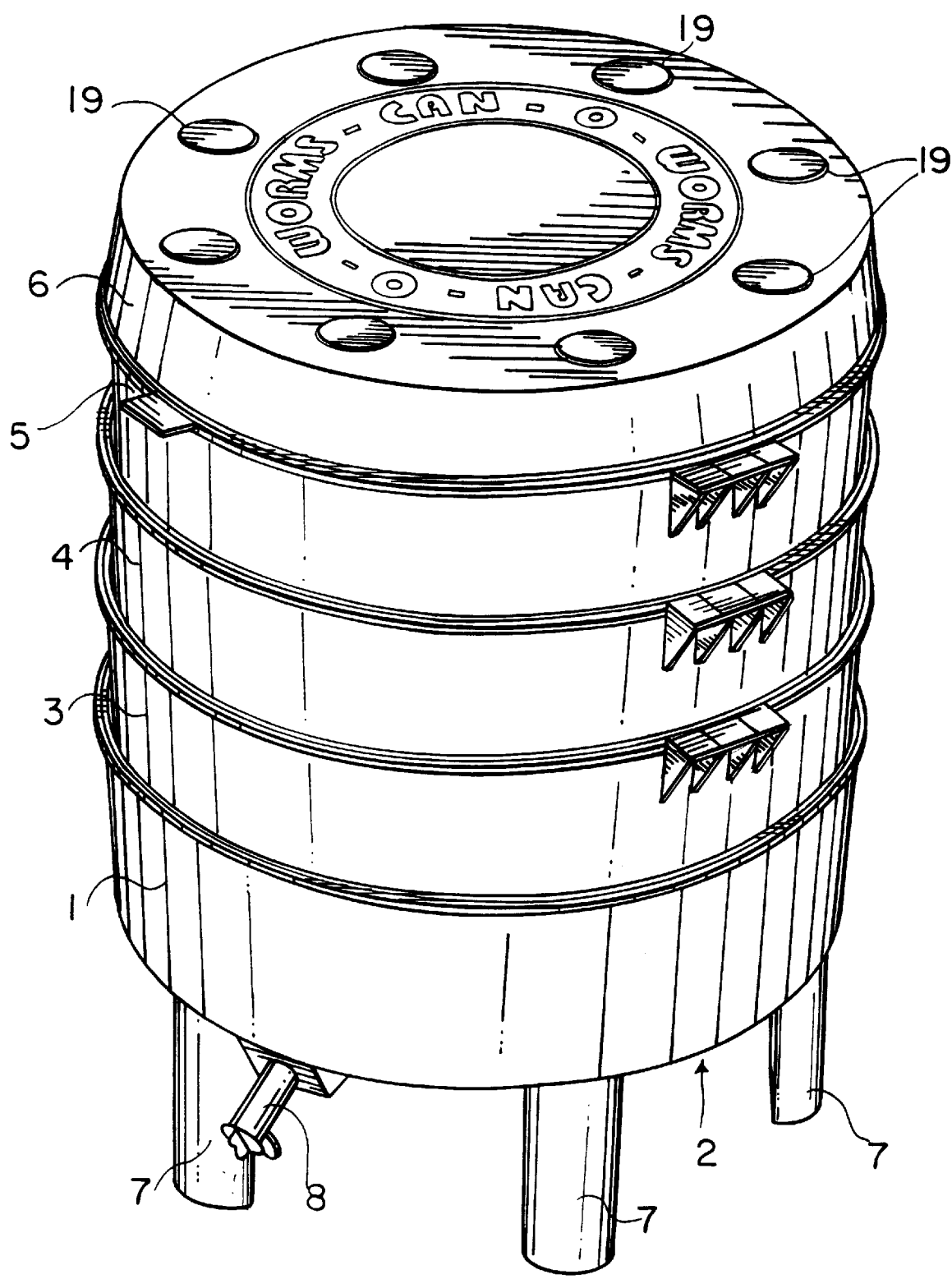
FIG. 1 is a perspective view of apparatus for breaking down organic matter according to the invention.

In the preferred form of the invention apparatus for breaking down organic matter is provided in the form of a lower container 1 having a circular base 2 and an upwardly extending peripheral side wall 3. Nested above the lower container 1 are a plurality of further circular containers 3, 4 and 5 topped by a lid 6. Each of the containers, 3, 4 and 5 has holes in the base thereof permitting liquids to drain through the containers to the bottom container 1 and also to permit worms to move upwardly from one container to another. The operation of apparatus of this nature is described in co-pending Australian patent application 58295/94.

The apparatus is supported on a plurality of legs 7 and is also provided with a drain tap 8 allowing liquid collecting in the lower container 1 to be drained from the apparatus as desired.

The configuration of the lower container 1 can be more clearly seen in FIGS. 2 and 3 where the base 2 and cylindrical upwardly extending side wall 3 are clearly shown. The centre of the base 2 may be provided with a conical raised portion 9 for reinforcing the bottom of the container and assisting the flow of liquid from within the container to recessed portion 10 which provides a mount for the tap 8.

The legs 7 are supported in the container 1 by a plurality of sockets 11 such that the upper end of each leg is inserted into a corresponding socket. Each socket is cup-like in configuration and tapers inwardly and upwardly so that the upper end 12 of each socket has a lesser diameter than the lower end 13. The upper end 12 of each socket is provided with an array of foramina sized to allow air flow from the interior of the socket 13 to the interior of the container 1 through the foramina while inhibiting the ingress of insects. The location and configuration of the foramina can be seen at 11A in FIG. 2, given by way of example as this pattern is repeated in the upper ends of all the sockets 11.

Figure 4:
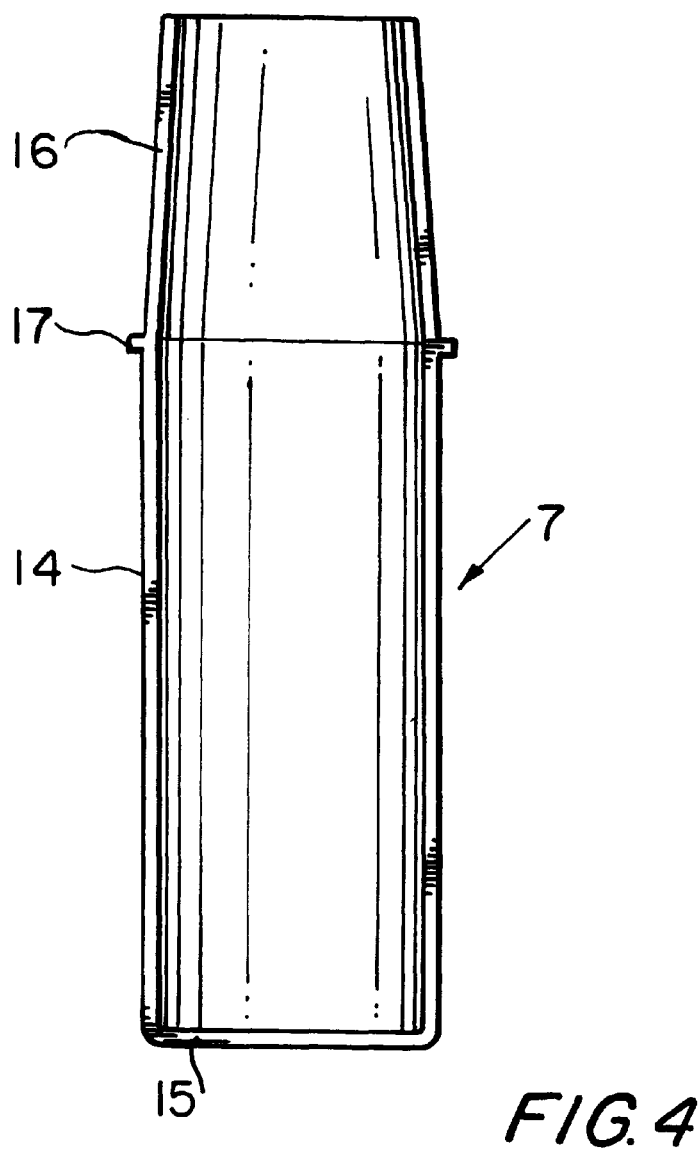
FIG. 4 is an elevation of one of the legs used in the apparatus according to the invention when removed from the container.
Figure 5:
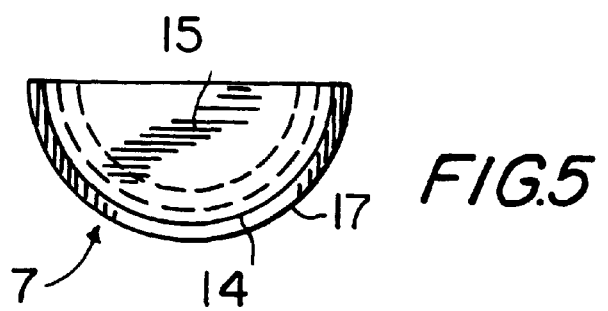
FIG. 5 is an underside view of the leg shown in FIG. 4.

Each leg 7 is typically semi-circular in shape and hollow in cross section as can be seen in FIG. 5 and comprises a peripheral wall 14 and a planar semi-circular bottom 15 adapted to rest on the ground or other suitable surface. The concavity of each semi-circular leg forms an open channel like duct within the leg. The upper end 16 of each leg is tapered inwardly as shown in FIG. 4 and provided with a locating flange 17 to enable the leg to be engaged in a corresponding socket 11. To orientate the leg correctly within the socket, each socket may be provided with a pair of inwardly extending diametrically opposed vertical ribs 18 to locate each leg such that the concavity of the semi-circular configuration faces inwardly toward the centre 19 of the lower container 1.

In use, when the apparatus is assembled as shown in FIG. 1, air flow from any direction, e.g. by way of breeze, passing over the apparatus is directed at the concave portion of one or more of the legs 7 due to the fact that the legs all face different directions. The air flow caught in this manner, due to local air pressure, passes upwardly within the leg into the upper tapered portion 16 and therefore into the corresponding socket 11 where it then passes through the foramina in the upper end of the socket and into the interior of the lower container 1. Because the foramina in the upper parts of the sockets 11 are raised a significant distance above the base 2 of the container 1, the accumulation of the material within the container 1 does not block the foramina and air flow can then occur at all phases of operation.

In the particular form of apparatus shown in FIG. 1, air flow passing into the lower container as described above can pass upwardly through the successive containers 3, 4 and 5 to be ultimately exhausted through vents 19 in the upper surface of the lid 6.

Although the container has been described as being cylindrical in nature with five legs equispaced about the perimeter of the base, it will be appreciated that the container could be any other suitable shape with other number of legs. For example, the container could be square or rectangular with a leg at each corner. Similarly the legs could be of any other convenient cross-section, incorporating an open channel-like duct.

In this manner a very effective form of ventilation for organic matter breakdown is simply provided in apparatus of the type described above. The ventilation not only assists aerobic breakdown of organic matter but also promotes the well being and breeding of worms on the organic matter within the apparatus.

What is claimed is:

1. Apparatus for breaking down organic matter comprising a container having a base and upwardly extending peripheral side walls, supported on a plurality of legs, characterised by the provision of an open channel-shaped duct within each leg, each leg being mounted to the container such that air can flow from the duct to the interior of the container, providing ventilation.

2. Apparatus as claimed in claim 1 wherein each leg is mounted in a corresponding socket in the base of the container.

3. Apparatus as claimed in claim 2 wherein each socket has one or more openings in the upper part thereof allowing air to pass from the duct in a leg engaged in the socket, into the container.

4. Apparatus as claimed in claim 3 wherein the openings comprise an array of foramina sized to allow air flow while inhibiting the ingress of insects.

5. Apparatus as claimed in claim 1 wherein the legs are orientated such that at least one open channel-shaped duct is exposed to horizontal air movement passing across the legs in any direction.

6. Apparatus as claimed in claim 1 wherein the legs are located around the perimeter of the base and wherein each open channel-shaped duct faces the centre of the base.

7. Apparatus as claimed in claim 1 wherein each channel-shaped duct extends longitudinally over the length of the corresponding leg.

8. Apparatus as claimed in claim 1 wherein the container is drum-shaped with a circular base and cylindrical side walls, and wherein five said legs are provided, substantially equispaced around the perimeter of the base.

9. Apparatus as claimed in claim 1 wherein each leg is substantially semi-circular and hollow in cross-section.

10. Apparatus as claimed in claim 1 wherein the container is provided with a lid having ventilation outlets therein.

* * * * *